(12) United States Patent
Futatsugi et al.

(10) Patent No.: US 10,537,225 B2
(45) Date of Patent: Jan. 21, 2020

(54) MARKING METHOD AND RESECTING METHOD

(71) Applicant: OLYMPUS CORPORATION, Tokyo (JP)

(72) Inventors: Yasuyuki Futatsugi, Hachioji (JP); Shigeru Imai, Hachioji (JP); Shin Hirashima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 388 days.

(21) Appl. No.: 15/361,572

(22) Filed: Nov. 28, 2016

(65) Prior Publication Data

US 2018/0146845 A1    May 31, 2018

(51) Int. Cl.
*A61B 1/00* (2006.01)
*A61B 18/00* (2006.01)
*A61B 1/04* (2006.01)
*A61B 1/06* (2006.01)
*A61B 1/267* (2006.01)

(52) U.S. Cl.
CPC ........ *A61B 1/00009* (2013.01); *A61B 1/0005* (2013.01); *A61B 1/043* (2013.01); *A61B 1/0638* (2013.01); *A61B 1/267* (2013.01); *A61B 2018/00571* (2013.01)

(58) Field of Classification Search
CPC ...... A61B 1/00009; A61B 1/043; A61B 90/39
USPC ........................................................ 606/116
See application file for complete search history.

(56) References Cited

U.S. PATENT DOCUMENTS

| 5,507,287 | A | * | 4/1996 | Palcic | A61B 1/043 |
|---|---|---|---|---|---|
| | | | | | 356/318 |
| 6,174,291 | B1 | * | 1/2001 | McMahon | A61B 5/0084 |
| | | | | | 600/564 |
| 2002/0021355 | A1 | * | 2/2002 | Utsui | A61B 1/043 |
| | | | | | 348/65 |
| 2014/0276810 | A1 | * | 9/2014 | Raybin | A61B 18/14 |
| | | | | | 606/46 |
| 2016/0015855 | A1 | | 1/2016 | Nohara et al. | |

FOREIGN PATENT DOCUMENTS

JP    2016-514108 A    5/2016

* cited by examiner

*Primary Examiner* — Aaron B Fairchild
(74) *Attorney, Agent, or Firm* — Scully, Scott, Murphy & Presser, P.C.

(57) ABSTRACT

A marking method includes: a step of irradiating, with first light (narrow band light) from an endoscope, an observation target site not suitable for spray of a coloring agent in a subject; a step of picking up an image of, through the endoscope, second light (reflected light of the narrow band light) generated at the observation target site through irradiation of the observation target site with the narrow band light; a step of displaying an image in which a site suspected to be a tumor is highlighted by generating the image based on the second light received through the endoscope; and a step of providing a tissue denatured portion around the site suspected to be a tumor by using an energy radiation device while the displayed image is observed.

10 Claims, 12 Drawing Sheets

MARKING METHOD AND RESECTING METHOD

BACKGROUND OF THE INVENTION

1. Field of the Invention

The present invention relates to a marking method and a resecting method performed through an endoscope.

2. Description of the Related Art

Conventionally, various kinds of less invasive examinations and operations by using an endoscope have been performed in a medical field. A surgeon inserts the endoscope into a body cavity, observes an object, an image of which is picked up by an image pickup apparatus provided at a distal end portion of an insertion portion of the endoscope, and can perform, as necessary, treatment on a lesion by using, for example, a treatment instrument inserted through a treatment instrument insertion channel.

When a lesion such as a tumor is to be resected in treatment using such an endoscope, a known method sprays various kinds of coloring agents onto the subject to make the boundary of the lesion distinguishable and provides marks such as dots around a target focus made distinguishable through the spraying of the coloring agents.

For example, Japanese Patent Application Laid-Open Publication No. 2016-514108 discloses, in endoscopic resecting of mucous membrane of a gastrointestinal system, a marking method of spraying indigocarmine pigment, specifying surface-raised early stomach cancer on the lesser curvature of a lower body, and providing marking with dots around a target focus using a precut knife to make the boundary of the cancer distinguishable.

For example, a widely-known marking method for a laryngopharynx performs iodine staining on a subject, and then performs marking under a white light source by using an iodine-stained site and an unstained site as determination criteria.

SUMMARY OF THE INVENTION

A marking method according to an aspect of the present invention includes: a step of inserting an endoscope into a subject; a step of irradiating, with first light from the endoscope, an observation target site not suitable for spray of a coloring agent in the subject; a step of picking up an image of, through the endoscope, second light generated at the observation target site through irradiation of the observation target site with the first light; a step of displaying an image in which a site suspected to be a tumor is highlighted by generating the image based on the second light received through the endoscope; and a step of providing a point-like, dotted-line-like, or linear tissue denatured portion around the site suspected to be a tumor by using an energy radiation device while the image is observed.

A resecting method according to another aspect of the present invention includes a step of resecting the site suspected to be a tumor by referring to the tissue denatured portion provided by the marking method.

DETAILED DESCRIPTION OF THE PREFERRED EMBODIMENTS

Figure 1:
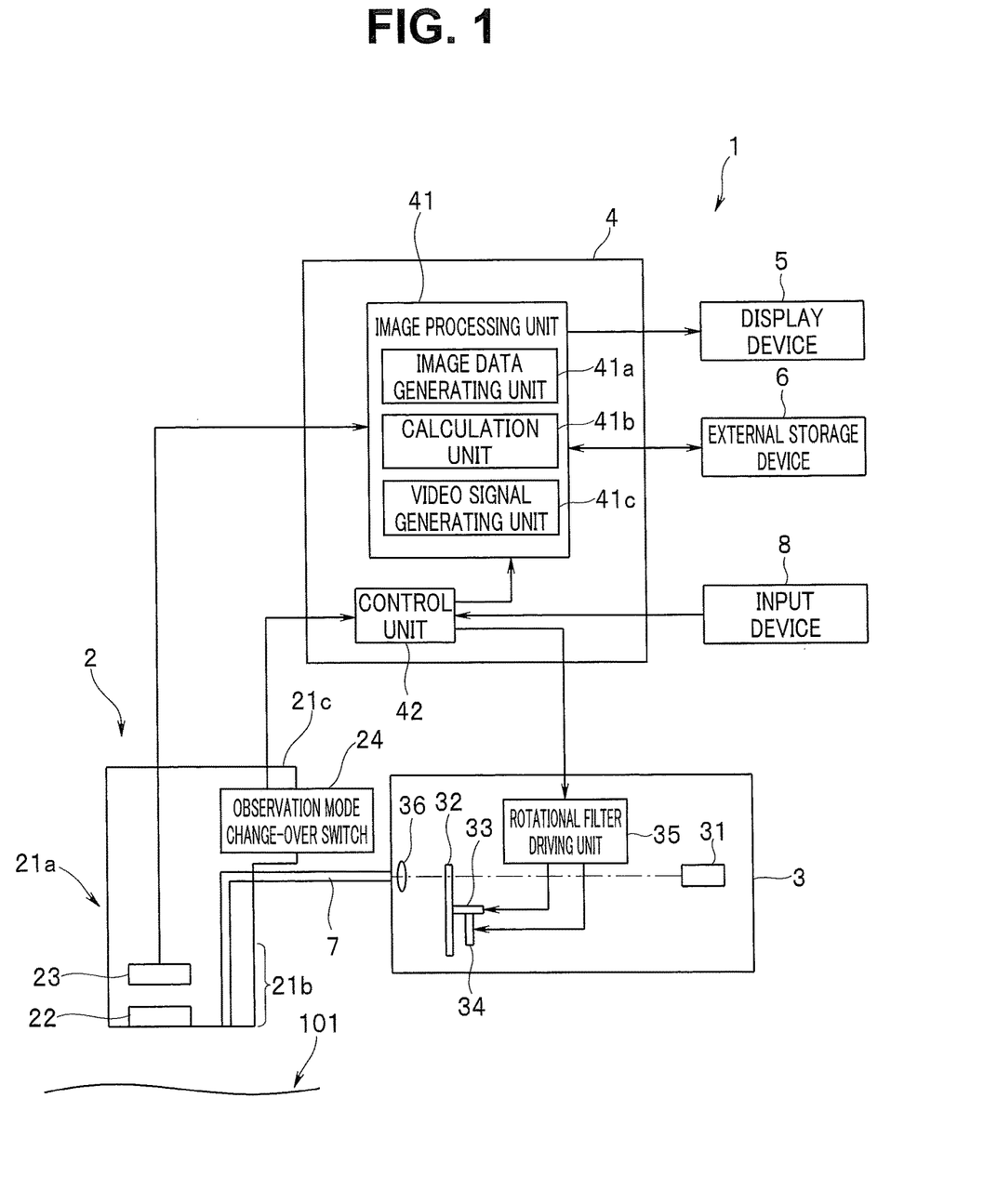
FIG. 1 is a diagram illustrating an exemplary configuration of a main part of an endoscope apparatus according to a first embodiment of the present invention.
Figure 2:
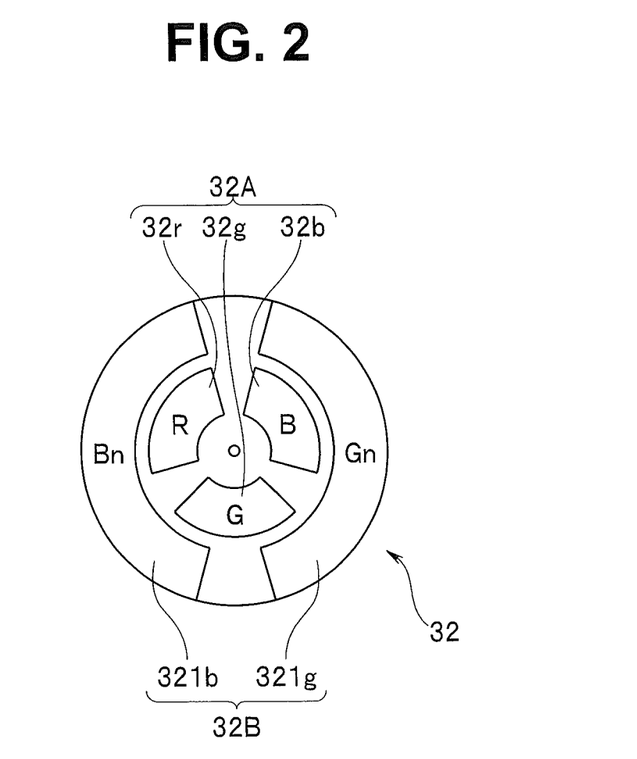
FIG. 2 is a diagram illustrating an exemplary configuration of a rotational filter included in a light source device according to the first embodiment of the present invention.
Figure 3:
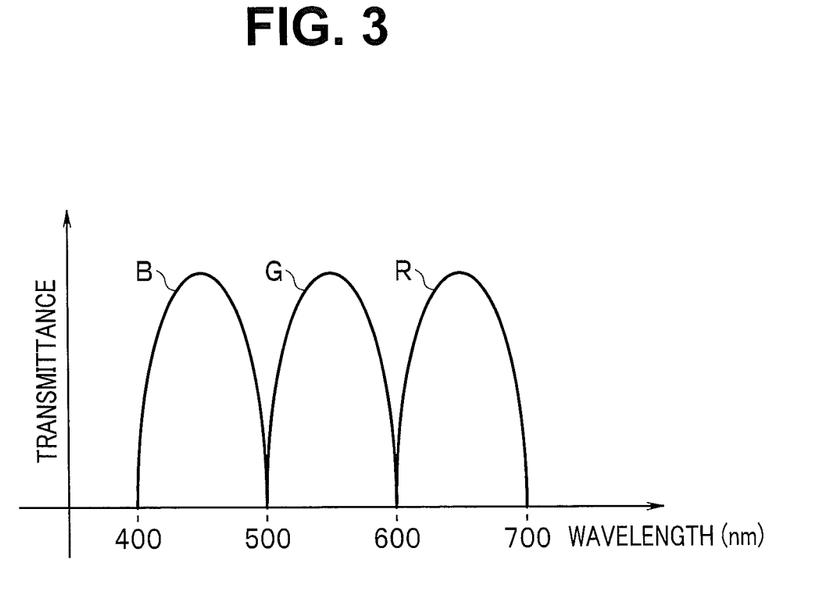
FIG. 3 is a diagram illustrating an exemplary transmittance characteristic of each filter included in a first filter group according to the first embodiment of the present invention.
Figure 4:
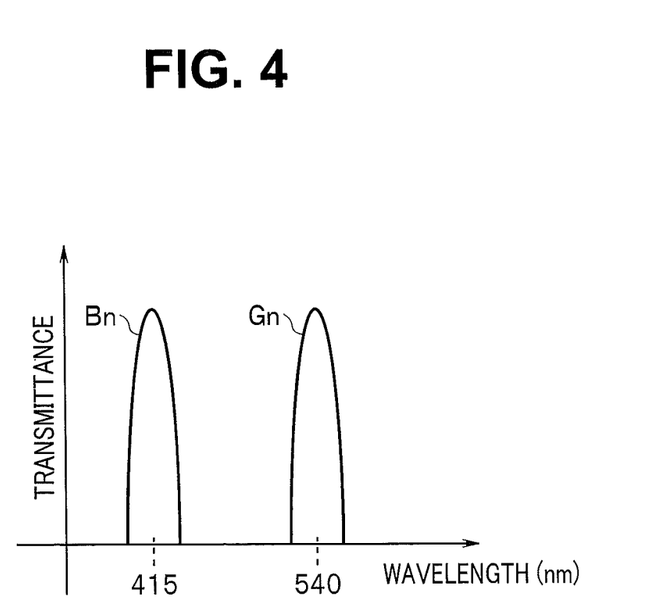
FIG. 4 is a diagram illustrating an exemplary transmittance characteristic of each filter included in a second filter group according to the first embodiment of the present invention.
Figure 5:
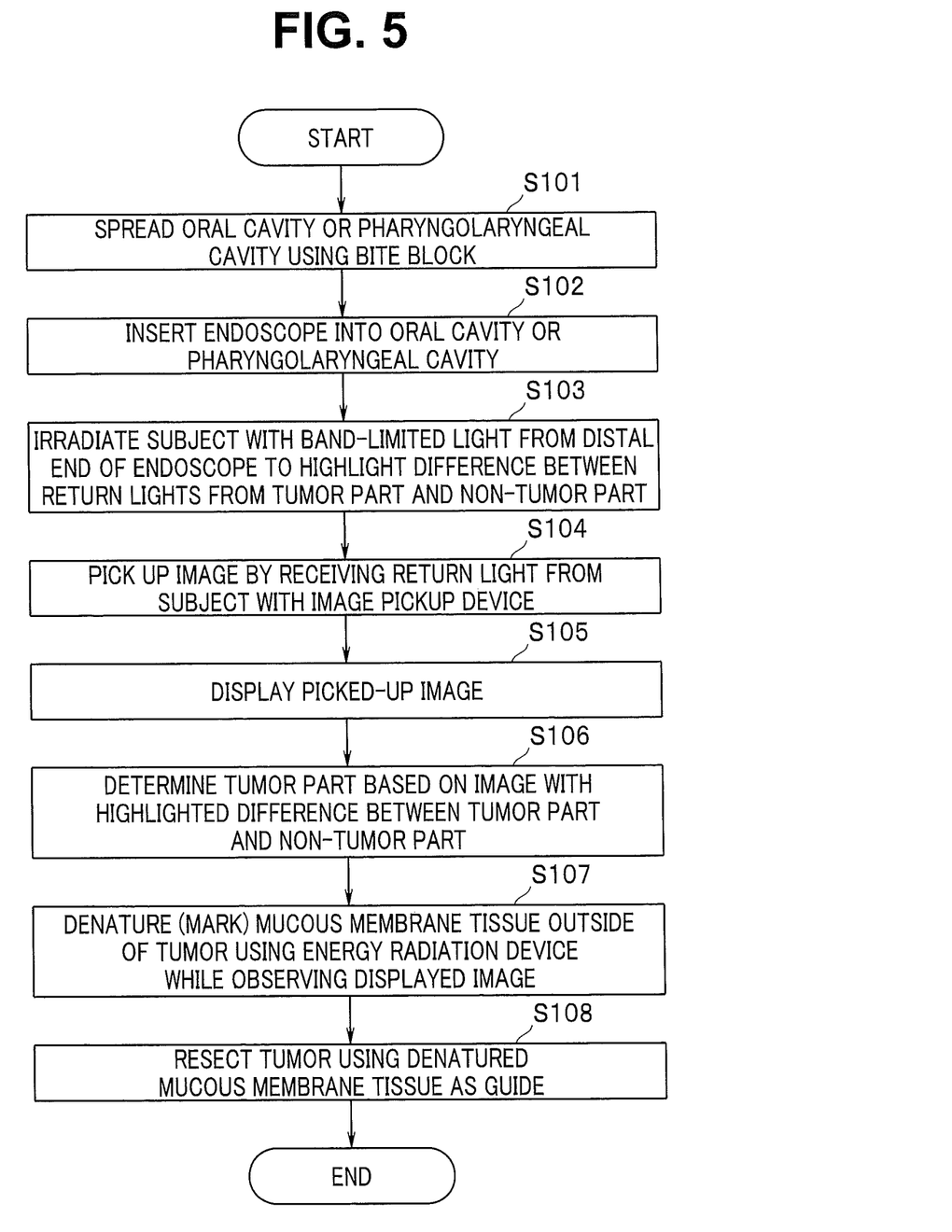
FIG. 5 is a flowchart illustrating an exemplary method of resecting a lesion in a laryngopharynx according to the first embodiment of the present invention.
Figure 6:
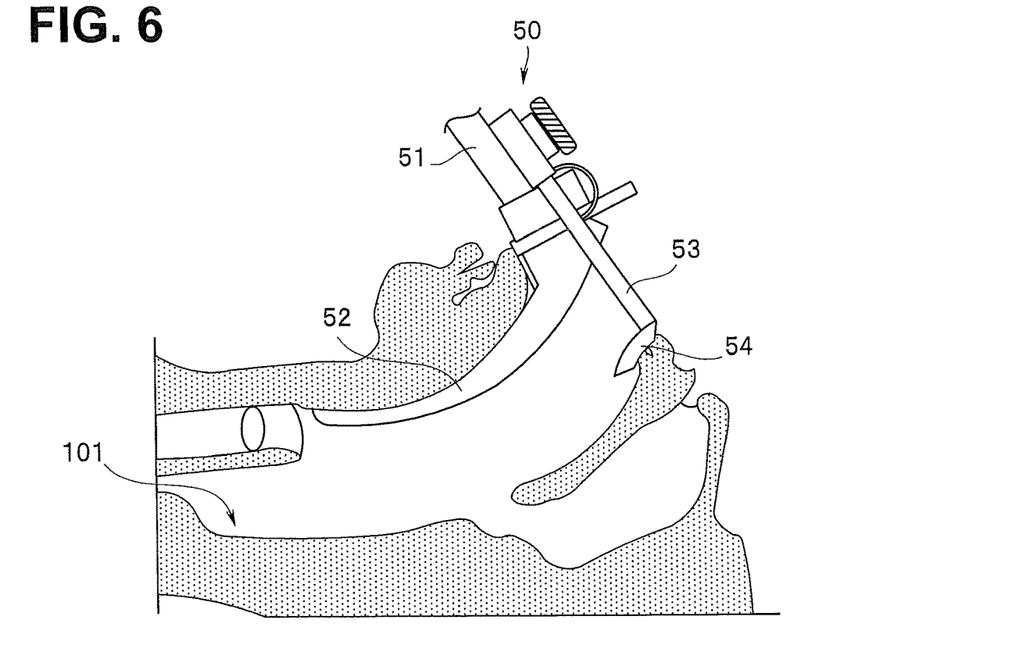
FIG. 6 is a diagram illustrating an exemplary state in which a pharyngolaryngeal cavity is spread using a bite block according to the first embodiment of the present invention.
Figure 7:
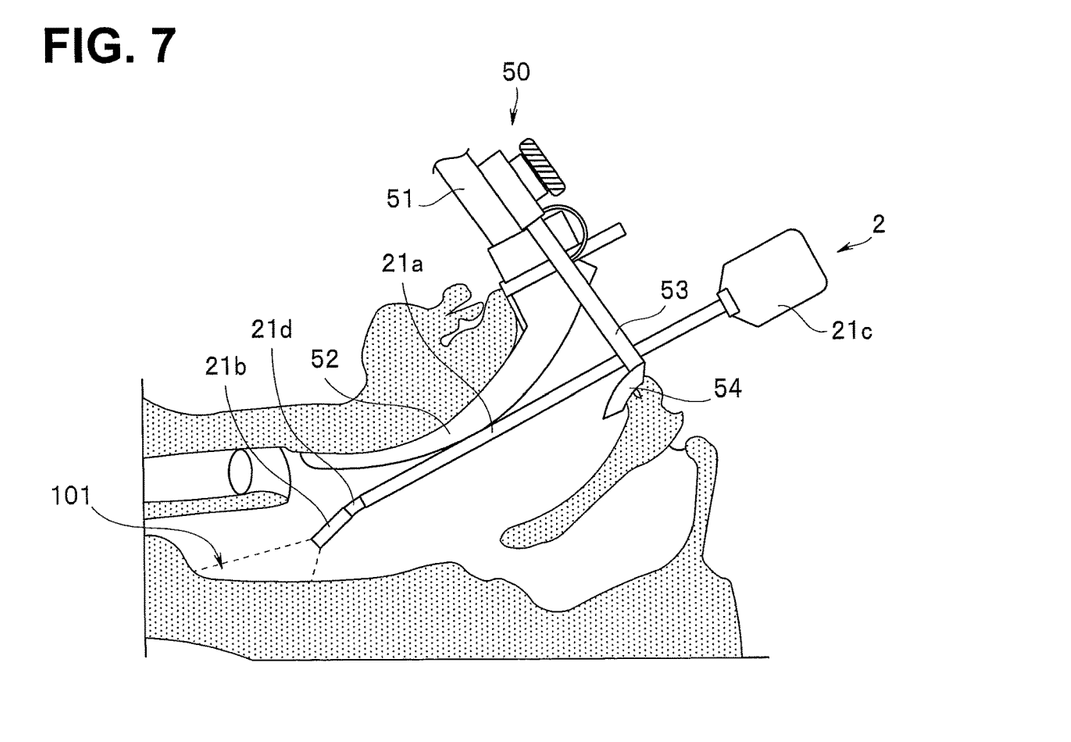
FIG. 7 is a diagram illustrating an exemplary state in which an endoscope is inserted into the pharyngolaryngeal cavity to irradiate a subject with light according to the first embodiment of the present invention.
Figure 8:
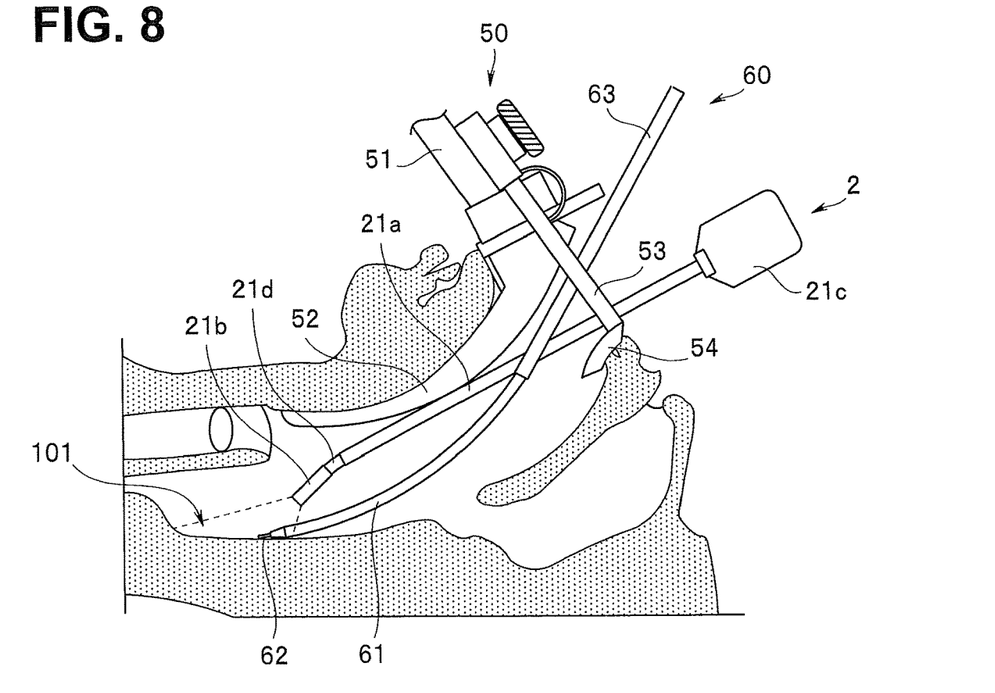
FIG. 8 is a diagram illustrating an exemplary state in which marking is provided to the subject according to the first embodiment of the present invention.
Figure 9:
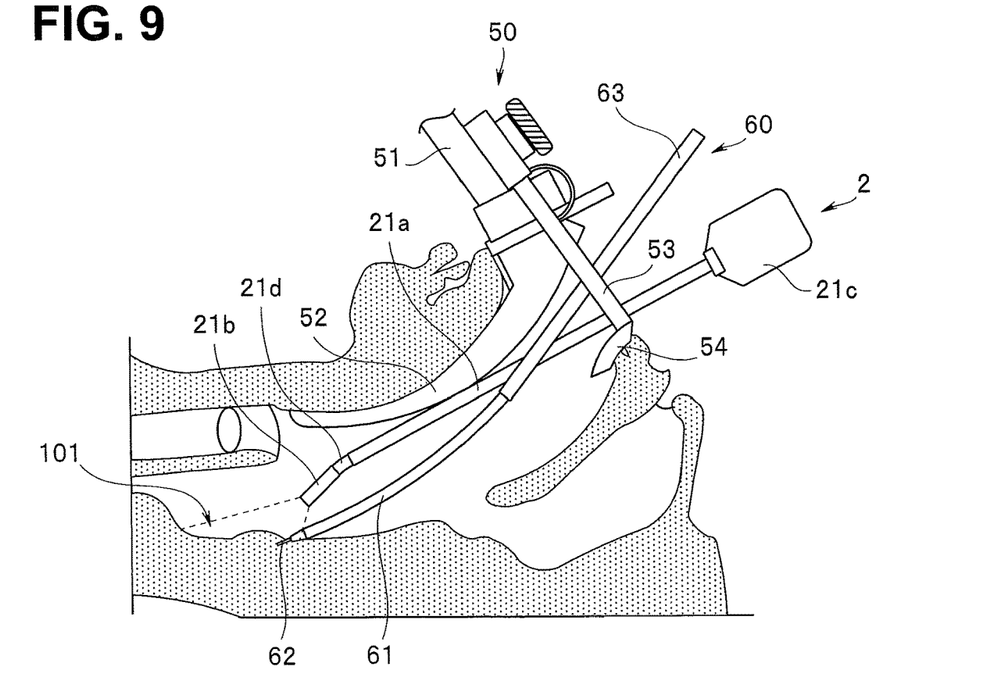
FIG. 9 is a diagram illustrating an exemplary state in which a tumor is resected using the marking as a guide according to the first embodiment of the present invention.
Figure 10:
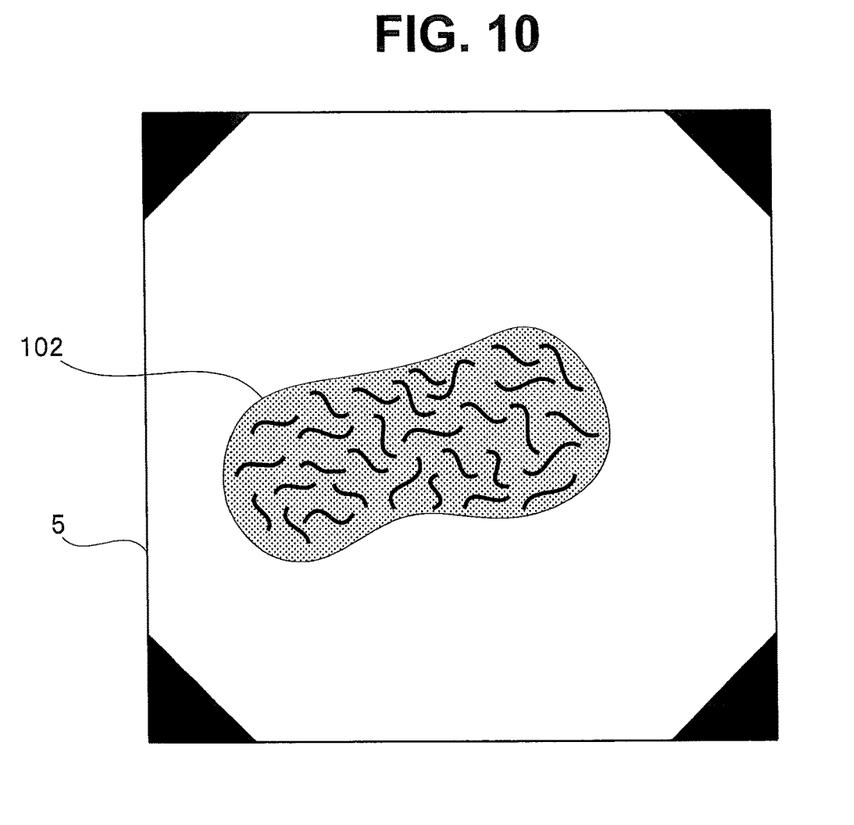
FIG. 10 is a diagram illustrating an exemplary image displayed on a display device according to the first embodiment of the present invention.
Figure 11:
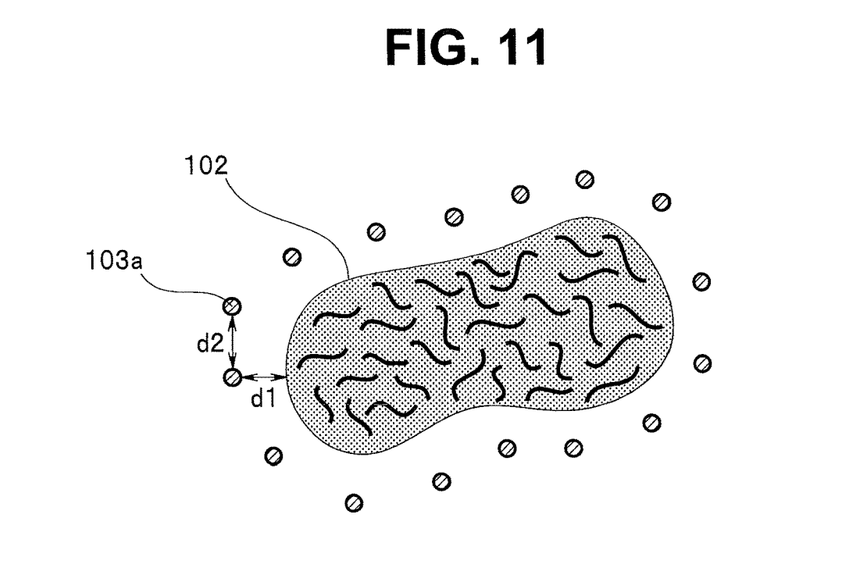
FIG. 11 is a diagram illustrating an exemplary state in which point marks are provided outside of the tumor according to the first embodiment of the present invention.
Figure 12:
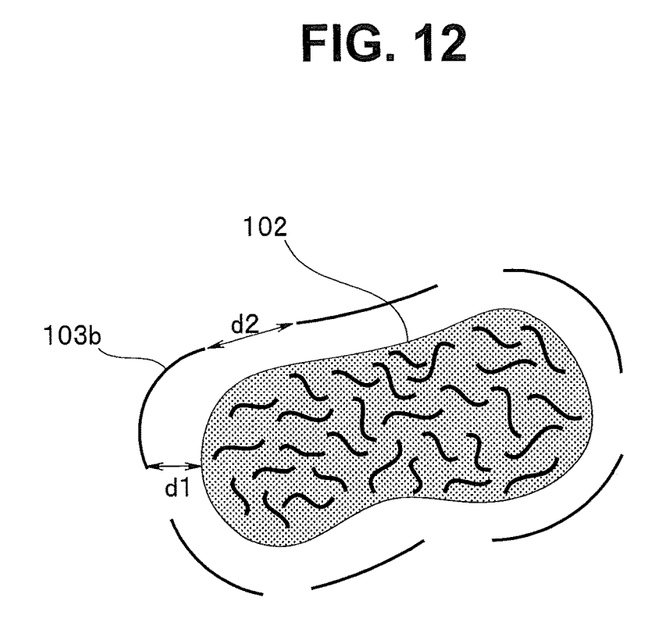
FIG. 12 is a diagram illustrating an exemplary state in which dotted line marks are provided outside of the tumor according to the first embodiment of the present invention.
Figure 13:
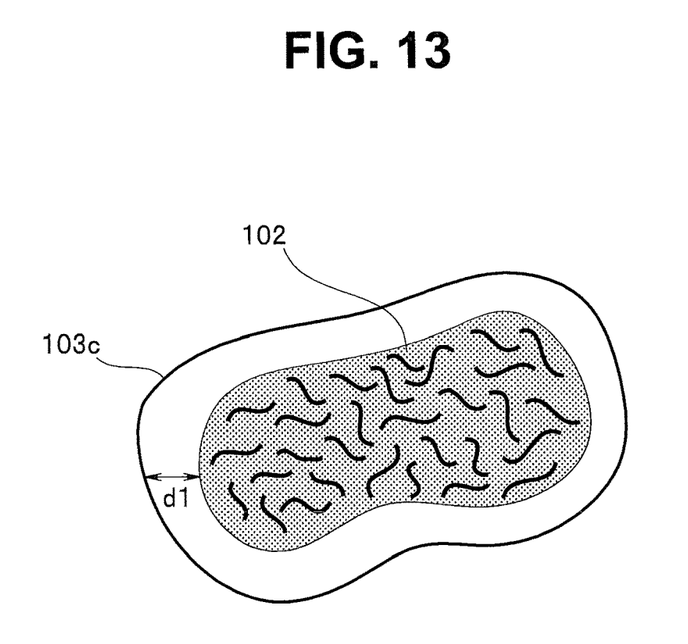
FIG. 13 is a diagram illustrating an exemplary state in which line marks are provided outside of the tumor according to the first embodiment of the present invention.

Embodiments of the present invention will be described below with reference to the accompanying drawings. FIGS. 1 to 12 illustrate a first embodiment of the present invention. FIG. 1 is a diagram illustrating an exemplary configuration of a main part of an endoscope apparatus. FIG. 2 is a diagram illustrating an exemplary configuration of a rotational filter included in a light source device. FIG. 3 is a diagram illustrating an exemplary transmittance characteristic of each filter included in a first filter group. FIG. 4 is a diagram illustrating an exemplary transmittance characteristic of each filter included in a second filter group. FIG. 5 is a flowchart illustrating an exemplary method of resecting a lesion in a laryngopharynx. FIG. 6 is a diagram illustrating an exemplary state in which a pharyngolaryngeal cavity is spread using a bite block. FIG. 7 is a diagram illustrating an exemplary state in which an endoscope is inserted into the pharyngolaryngeal cavity to irradiate a subject with light. FIG. 8 is a diagram illustrating an exemplary state in which marking is provided to the subject. FIG. 9 is a diagram illustrating an exemplary state in which a tumor is resected by using the marking as a guide. FIG. 10 is a diagram illustrating an exemplary image displayed on a display device. FIG. 11 is a diagram illustrating an exemplary state in which point marks are provided outside of the tumor. FIG. 12 is a diagram illustrating an exemplary state in which dotted line marks are provided outside of the tumor. FIG. 13 is a diagram illustrating an exemplary state in which line marks are provided outside of the tumor.

The present embodiment describes, as a method of marking and a method of resecting a lesion of a subject, a method of marking and a method of resecting a lesion such as a tumor in, for example, an oral cavity or a pharyngolaryngeal cavity (hereinafter, these are collectively referred to as "the pharyngolaryngeal cavity or the like" as appropriate).

A widely used method for the pharyngolaryngeal cavity or the like distinguishes (for example, performs iodine staining on) a lesion by spraying a coloring agent to mark circumference of the distinguished lesion, but the iodine staining of the pharyngolaryngeal cavity or the like has a risk of complication such as edema in some cases. Thus, the pharyngolaryngeal cavity or the like is basically one of sites not suitable for spraying of a coloring agent.

The present embodiment first describes an endoscope apparatus 1 used to perform marking and resecting of a lesion. As illustrated in FIG. 1, the endoscope apparatus 1 includes an endoscope 2 inserted into a body cavity of an examinee to acquire an image through image pickup of, as an object, a living tissue 101 such as a mucous membrane existing in the body cavity and output the image as a signal, a light source device 3 configured to emit illumination light with which the living tissue 101 is illuminated, a processor 4 configured to provide various kinds of processing to the signal output from the endoscope 2, a display device 5 configured to display an image in accordance with a video signal from the processor 4, an external storage device 6 configured to store therein an output signal in accordance with a result of processing at the processor 4, and an input device 8 capable of providing the processor with an instruction in response to an input operation.

The endoscope 2 includes an insertion portion 21a having a shape and a size that allow insertion into the body cavity (pharyngolaryngeal cavity) of the examinee, a distal end portion 21b provided on a distal end side of the insertion portion 21a, and an operation portion 21c provided on a proximal end side of the insertion portion 21a. A light guide 7 for transmitting, to the distal end portion 21b, the illumination light emitted from the light source device 3 is inserted through inside of the insertion portion 21a. For example, as illustrated in FIGS. 7 to 9, the endoscope 2 according to the present embodiment is a rigid endoscope including, on the distal end side of the rigid insertion portion 21a, a bending portion 21d capable of changing a direction of the distal end portion 21b.

One end face (light incident end face) of the light guide 7 is detachably connected with the light source device 3. The other end face (light emitting end face) of the light guide 7 is disposed near an illumination optical system (not illustrated) provided to the distal end portion 21b of the endoscope 2. With such a configuration, the illumination light from the light source device 3 is emitted to the living tissue 101 as an observation target site through the light guide 7 being connected with the light source device 3, and the illumination optical system (not illustrated) provided to the distal end portion 21b.

The distal end portion 21b of the endoscope 2 is provided with an objective optical system 22 configured to form an optical image of an object, and a CCD 23 configured to acquire an image through image pickup of the optical image formed by the objective optical system 22. The operation portion 21c of the endoscope 2 is provided with an observation mode change-over switch 24 capable of providing an instruction for switching an observation mode to one of a normal light observation mode and a narrow band light observation mode.

The light source device 3 includes a white light source 31 including, for example, a xenon lamp, a rotational filter 32 configured to convert white light emitted from the white light source 31 into frame-sequential illumination light, a motor 33 configured to rotate the rotational filter 32, a motor 34 configured to move the rotational filter 32 and the motor 33 in a direction vertical to an emission light path of the white light source 31, a rotational filter driving unit 35 configured to drive the motors 33 and 34 under control of the processor 4, and a condenser optical system 36 configured to condense the illumination light passing through the rotational filter 32 and supply the condensed illumination light to the incident end face of the light guide 7. FIG. 2 is a diagram illustrating an exemplary configuration of the rotational filter included in the light source device.

The rotational filter 32 is shaped in a circular plate having a rotational axis at its center as illustrated in FIG. 2, and includes a first filter group 32A including a plurality of filters provided on an inner periphery side in a circumferential direction, and a second filter group 32B including a plurality of filters provided on an outer periphery side in the circumferential direction. When drive power of the motor 33 is transferred to the rotational axis, the rotational filter 32 rotates. Note that part of the rotational filter 32 except for a part in which the filters of the first filter group 32A and the second filter group 32B are disposed is formed of a light-shielding member.

The first filter group 32A includes a R filter 32r, a G filter 32g, and a B filter 32b respectively provided on the inner periphery side of the rotational filter 32 in the circumferential direction, the R filter 32r being configured to transmit light of a red wavelength band, the G filter 32g being configured to transmit light of a green wavelength band, and the B filter 32b being configured to transmit light of a blue wavelength band.

As illustrated in, for example, FIG. 3, the R filter 32r has a configuration for mainly transmitting light (R light) having a wavelength of 600 nm to 700 nm. As illustrated in, for example, FIG. 3, the G filter 32g has a configuration for mainly transmitting light (G light) having a wavelength of 500 nm to 600 nm. As illustrated in, for example, FIG. 3, the B filter 32b has a configuration for mainly transmitting light (B light) having a wavelength of 400 nm to 500 nm.

That is, wide band light for the normal light observation mode is generated when the white light emitted from the white light source 31 passes through the first filter group 32A.

The second filter group 32B includes a Bn filter 321b and a Gn filter 321g respectively provided on the outer periphery side of the rotational filter 32 in the circumferential direction, the Bn filter 321b being configured to transmit blue narrow band light, and the Gn filter 321g being configured to transmit green narrow band light.

As illustrated in, for example, FIG. 4, the Bn filter 321b is configured to transmit light (Bn light) having a central wavelength set to be near 415 nm and a band narrower than a band of the B light. As illustrated in, for example, FIG. 4, the Gn filter 321g is configured to transmit light (Gn light) having a central wavelength set to be near 540 nm and a band narrower than a band of the G light.

That is, narrow band light of a plurality of bands is generated for the narrow band light observation mode by discretization of, through the second filter group 32B, the white light emitted from the white light source 31.

The processor 4 has functionality of a medical image processing apparatus. More specifically, the processor 4 includes an image processing unit 41 and a control unit 42. The image processing unit 41 includes an image data generating unit 41a, a calculation unit 41b, and a video signal generating unit 41c.

The image data generating unit 41a of the image processing unit 41 generates image data in accordance with the image obtained at the CCD 23 by providing the output signal from the endoscope 2 with processing such as noise removal and A/D conversion.

The calculation unit 41b of the image processing unit 41 reads as appropriate, from the external storage device 6 or a memory (not illustrated), a computer program for performing predetermined processing on the image data generated by the image data generating unit 41a, and executes the computer program.

The video signal generating unit 41c of the image processing unit 41 generates a video signal by providing processing such as gamma conversion and D/A conversion to the image data provided with the processing by the calculation unit 41b, and outputs the video signal.

The control unit 42 is configured to perform control on the image processing unit 41 based on the instruction provided from the input device 8. The control unit 42 is also configured to perform control on the light source device 3 based on the instruction provided from the observation mode change-over switch 24.

More specifically, for example, when having detected based on the instruction provided from the observation mode change-over switch 24 that switching to the normal light observation mode is instructed, the control unit 42 performs, on the rotational filter driving unit 35, control for causing the light source device 3 to emit the wide band light for the normal light observation mode. Then, the rotational filter driving unit 35 operates, based on the control by the control unit 42, the motor 34 to interpose the first filter group 32A into the emission light path of the white light source 31 and retract the second filter group 32B from the emission light path of the white light source 31.

For example, when having detected based on the instruction provided from the observation mode change-over switch 24 that switching to the narrow band light observation mode is instructed, the control unit 42 performs, on the rotational filter driving unit 35, control for causing the light source device 3 to emit the narrow band light of a plurality of bands for the narrow band light observation mode. Then, the rotational filter driving unit 35 operates, based on the control by the control unit 42, the motor 34 to interpose the second filter group 32B into the emission light path of the white light source 31, and retract the first filter group 32A from the emission light path of the white light source 31.

That is, with the above-described configuration of the endoscope apparatus 1, when the normal light observation mode is selected, an image (normal light image) having substantially the same colors as colors of the object when observed with bare eyes can be displayed on the display device 5, and in addition, image data corresponding to the image displayed on the display device 5 can be stored in the external storage device 6.

With the above-described configuration of the endoscope apparatus 1, when the narrow band light observation mode is selected, an image (narrow band light image) in which a blood vessel included in the living tissue 101 is highlighted can be displayed on the display device 5, and in addition, image data corresponding to the image displayed on the display device 5 can be stored in the external storage device 6.

The input device 8, which has a function of an input unit, includes, for example, a mouse and/or a keyboard, and is configured to perform, to the processor 4, an instruction in response to an input operation.

In the present embodiment, when marking and resecting of a lesion are performed, for example, a retractor 50 is used as a bite block to spread the pharyngolaryngeal cavity or the like.

The retractor 50 includes an arm portion 51 supported by, for example, an operation bed (not illustrated), a blade portion 52 supported in a tiltable manner by a distal end of the arm portion 51, and a teeth receiving portion 54 provided to a frame portion 53 movable relative to the arm portion 51.

The retractor 50 is inserted into an oral cavity so that the blade portion 52 is in contact with lower teeth (mandible side) of a subject and the teeth receiving portion 54 is in contact with upper teeth (upper mandible side) of the subject, and then the blade portion 52 and the teeth receiving portion 54 are operated in a direction of separation from each other, thereby spreading the pharyngolaryngeal cavity.

In the present embodiment, when marking and resecting of a lesion are performed, for example, a diathermy knife 60 is used as an energy radiation device. As illustrated in FIG. 8, the diathermy knife 60 includes, for example, an elongated insertion portion 61, a treatment unit 62 disposed at a distal end portion of the insertion portion 61, and an operation portion 63 disposed at a proximal end portion of the insertion portion 61. The diathermy knife 60 can cause high-frequency current to flow from the treatment unit 62 to the subject to perform, for example, dissection through heating of cells to cause explosion and vaporization, and coagulation (tissue denaturation) through coagulation of protein by evaporating fluid of cells.

The following describes a method of resecting a lesion such as a tumor with reference to FIG. 5. The resecting method according to the present embodiment includes a method of marking the lesion.

In the resecting method, first at step S101, a surgeon or the like (hereafter, "surgeon") spreads an oral cavity or a pharyngolaryngeal cavity using a bite block. In the present embodiment, more specifically, the surgeon spreads the pharyngolaryngeal cavity using the retractor 50 (refer to FIG. 6).

At the subsequent step S102, the surgeon inserts the insertion portion 21a of the endoscope 2 into the oral cavity or the pharyngolaryngeal cavity. In the present embodiment, more specifically, the surgeon selects, for example, the normal light observation mode, and inserts the insertion portion 21a of the endoscope 2 into the pharyngolaryngeal cavity through the oral cavity, while observing the normal light image displayed on the display device 5 (refer to FIG. 7).

Thereafter, the surgeon operates the observation mode change-over switch 24 of the endoscope 2 to select the narrow band light observation mode as the observation mode of the endoscope apparatus 1, and causes the display device 5 to display an image in which a difference between a tumor part and a non-tumor part is highlighted (steps S103 to S105).

That is, when the narrow band light observation mode is selected by the surgeon, an observation target site of the subject is irradiated with band-limited narrow band light (first light) from the distal end portion 21b of the endoscope 2 to highlight a difference between return lights from the tumor part and the non-tumor part (step S103). More specifically, the observation target site of the subject is irradiated with special light (refer to FIG. 4) made of blue and green narrow band lights.

Then, an image is picked up by receiving and picking up an image of, through the CCD 23 provided to the distal end portion 21b of the endoscope 2, return light (second light) generated at the observation target site through irradiation of the observation target site with the narrow band light (step S104). More specifically, an image is picked up by picking up an image of, through the CCD 23, reflected light of the narrow band light with which the observation target site is irradiated.

Then, an image pickup signal based on the second light is processed by the image processing unit 41, and an image in which a site suspected to be a tumor is highlighted is displayed on the display device 5 (step S105). More specifically, since the narrow band light is absorbed by hemoglobin, an image, contrast of which is enhanced to make distinguishable a fine mucous membrane pattern and surficial blood vessels, is displayed on the display device 5. Accordingly, the site suspected to be a tumor is displayed on the display device 5 while being highlighted through dense fine blood vessels and the like (refer to FIG. 10).

At the subsequent step S106, the surgeon determines a tumor part 102 while observing the image displayed on the display device 5. That is, the surgeon specifically determines the tumor part 102 based on the image with a highlighted difference between the tumor part (site suspected to be a tumor) and the non-tumor part.

At the subsequent step S107, while observing the displayed image, the surgeon performs marking, by denaturing, with the diathermy knife 60 as the energy radiation device, mucous membrane tissue outside of a site determined to be the tumor part 102 (refer to FIG. 8).

In this case, for example, as illustrated in FIG. 11, the surgeon can provide a point-like tissue denatured portion 103a around the site determined to be the tumor part 102. More specifically, the surgeon can provide, at a distance d1 (d1=several millimeters approximately) outside of the site determined to be the tumor part 102, the tissue denatured portion (mark) 103a made of a sequence of points with an interval d2 (d2=several millimeters approximately).

Alternatively, for example, as illustrated in FIG. 12, the surgeon can provide a dotted-line-like tissue denatured portion 103b around the site determined to be the tumor part 102. More specifically, the surgeon can provide, at the distance d1 (d1=several millimeters approximately) outside of the site determined to be the tumor part 102, the tissue denatured portion (mark) 103b made of a sequence of lines with the interval d2 (d2=several millimeters approximately).

Alternatively, for example, as illustrated in FIG. 13, the surgeon can provide a linear tissue denatured portion 103c around the site determined to be the tumor part 102. More specifically, the surgeon can provide the linear tissue denatured portion (mark) 103c at the distance d1 (d1=several millimeters approximately) outside of the site determined to be the tumor part 102.

At the subsequent step S108, the surgeon resects the tumor using the denatured mucous membrane tissue as a guide (refer to FIG. 9). More specifically, the surgeon operates the observation mode change-over switch 24 of the endoscope 2 to select, for example, the normal light observation mode, and then resects the tumor part 102 along the mark by using the diathermy knife 60 while observing the normal light image displayed on the display device 5.

This marking method according to the embodiment includes: a step of irradiating, with the first light (narrow band light) from the endoscope 2, an observation target site not suitable for spray of a coloring agent in the subject; a step of picking up an image of, through the endoscope 2, the second light (reflected light of the narrow band light) generated at the observation target site through irradiation of the observation target site with the narrow band light; a step of displaying an image in which a site suspected to be a tumor is highlighted by generating the image based on the second light received through the endoscope 2; and a step of providing a tissue denatured portion around the site suspected to be a tumor by using the energy radiation device while the displayed image is observed. Accordingly, a site suspected to be a tumor can be appropriately determined and marked in a site such as the pharyngolaryngeal cavity or the like not suitable for spray of a coloring agent, without causing, for example, complication due to spray of the coloring agent.

The resecting method according to the embodiment may include a step of resecting the site suspected to be a tumor by referring to the tissue denatured portion provided by the above-described marking method. Accordingly, a site suspected to be a tumor can be appropriately determined and resected in a site such as the pharyngolaryngeal cavity or the like not suitable for spray of a coloring agent, without causing, for example, complication.

The present embodiment describes an exemplary method of performing marking and resecting of a tumor part through the narrow band light observation in which an image in which a site suspected to be a tumor is highlighted is generated by emitting the narrow band light as the first light and picking up an image of the second light as the return light. According to a modification, however, marking and resecting of a tumor part may be performed through special light observation using another special light (non-white light).

Note that, in each technology of the special light observation described below, the light source device 3 has a configuration different from the above-described configuration depending on used special light, but a light source device configured to emit various kinds of special light has a known configuration, and thus detailed description thereof will be omitted. In the technology of the special light observation described below, processing or the like at the calculation unit 41b is different from the above-described processing or the like, but various kinds of image processing are known, and thus detailed description thereof will be omitted.

For example, when tumor tissue of a subject is irradiated with blue excitation light (390 to 440 nm: first light), self-fluorescence (second light) attenuates as compared to a case of normal tissue. This characteristic can be utilized to perform marking and resecting of a tumor part by using a fluorescence observation technology of performing highlight display by representing a difference corresponding to the attenuation as color tone.

Alternatively, for example, marking and resecting of a tumor part may be performed by using an infrared light observation technology of performing highlight display of blood vessel and blood flow information on a mucous membrane deep portion, which is difficult to visually recognize in the normal light observation, by irradiating a subject with two infrared lights (790 to 820 nm, 905 to 970 nm: first light) as non-visible light and picking up an image of return light (second light).

Alternatively, for example, marking and resecting of a tumor part may be performed by using a narrow band light observation technology of displaying an image suitable for observation of a blood vessel and a surficial structure by performing image processing on a high-contrast signal obtained by irradiating a subject with short-wavelength laser light (first light) suitable for surficial blood vessel observation and picking up an image of return light (second light).

Alternatively, for example, marking and resecting of a tumor part may be performed by using a technology that performs image processing to enhance color separation of a red region (particular wavelength) on an image with increased contrast of blood inside of mucous membrane obtained by irradiating a subject with narrow band light observation laser (first light) while maintaining brightness of an image with white light laser (first light), and picking up an image of return light (second light), and extends saturation difference and chromaticity difference of a color close to the color of the mucous membrane to support diagnosis of inflammation.

Alternatively, for example, marking and resecting of a tumor part may be performed by using a technology that achieves improved visibility of a blood vessel, a duct, and a surficial structure by combining digital image processing on an image obtained by irradiating a subject with band-limited light (first light) and picking up an image of return light (second light).

Figure 14:
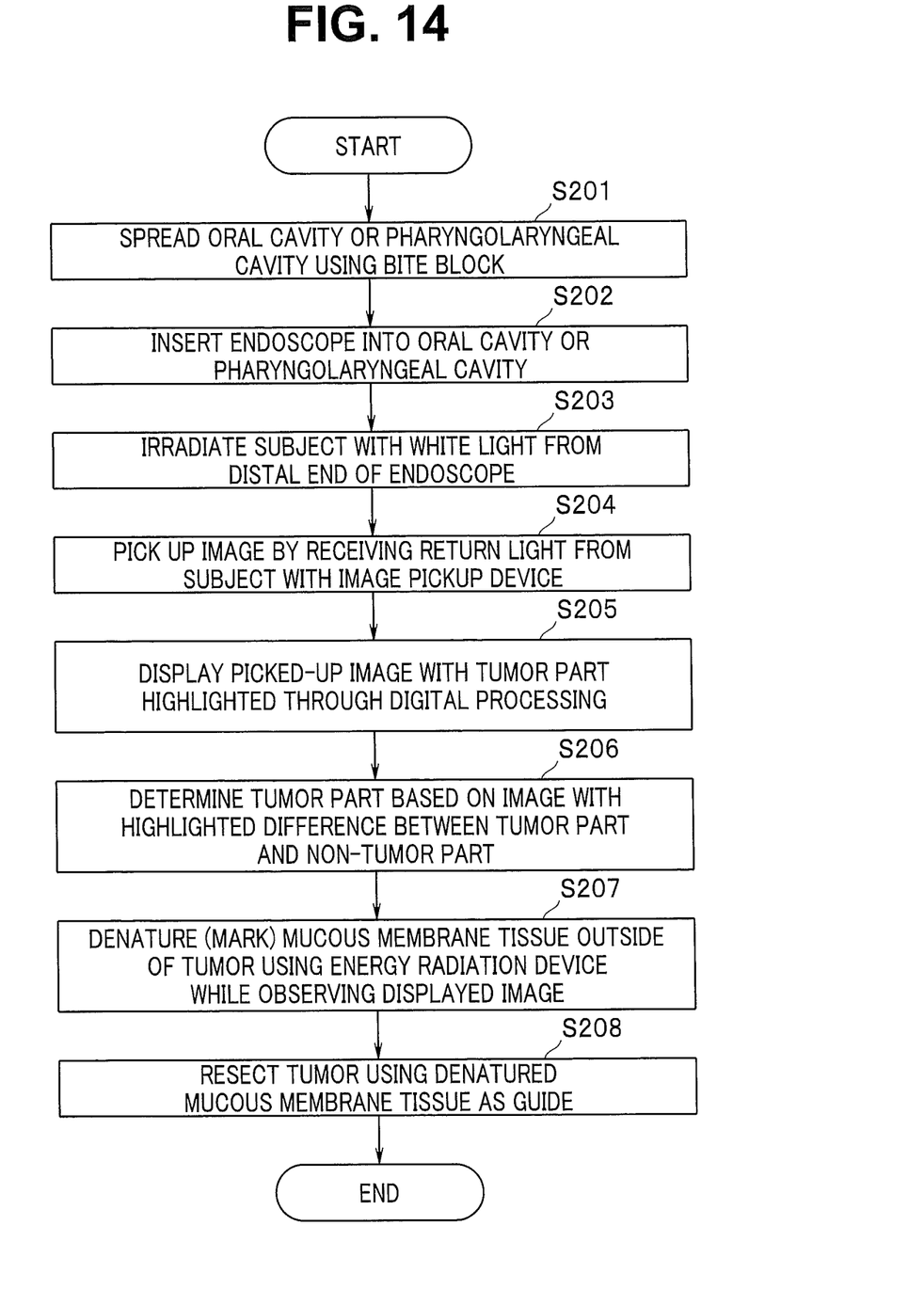
FIG. 14 is a flowchart illustrating an exemplary method of resecting a lesion in the laryngopharynx according to a second embodiment of the present invention.

FIG. 14 illustrates a second embodiment of the present invention, and is a flowchart illustrating an exemplary method of resecting a lesion in a laryngopharynx. Note that the present embodiment is different from the above-described first embodiment mainly in that a site suspected to be a tumor is highlighted by performing digital processing on an image obtained by irradiating a subject with non-special light (white light) as the first light and picking up an image of return light (second light) from the subject. Description of any other feature same as the feature of the above-described first embodiment will be omitted as appropriate.

Note that the observation mode change-over switch 24 according to the present embodiment can perform an instruction for switching the observation mode to one of the normal light observation mode and a highlighted image observation mode by digital image processing.

As illustrated in FIG. 14, in the resecting method according to the present embodiment, first at step S201, the surgeon spreads an oral cavity or a pharyngolaryngeal cavity using a bite block.

At the subsequent step S202, the surgeon selects, for example, the normal light observation mode, and inserts the insertion portion 21a of the endoscope 2 into the oral cavity or the pharyngolaryngeal cavity while observing a normal light image displayed on the display device 5.

Thereafter, the surgeon operates the observation mode change-over switch 24 of the endoscope 2 to select the highlighted image observation mode as the observation mode of the endoscope apparatus 1, and causes the display device 5 to display an image in which a difference between a tumor part and a non-tumor part is highlighted (steps S203 to S205).

That is, when the highlighted image observation mode is selected by the surgeon, the observation target site of the subject is continuously irradiated with white light (first light) from the distal end portion 21b of the endoscope 2 (step S203).

Then, an image is picked up by receiving and picking up an image of, through the CCD 23 provided to the distal end portion 21b of the endoscope 2, return light (second light) generated at the observation target site through irradiation of the observation target site with the white light (step S204).

Then, an image pickup signal based on the second light is digitally processed by the image processing unit 41, and an image in which a site suspected to be a tumor is highlighted is displayed on the display device 5 (step S205). More specifically, for example, the calculation unit 41b extracts a spectroscopic image of an optional wavelength component from a spectroscopic image that can be obtained through spectroscopic estimation processing, and restructures the image by allocating R, G, and B to the spectroscopic image, thereby generating an image in which a site suspected to be a tumor is highlighted and displaying the image on the display device 5.

At the subsequent step S206, the surgeon determines the tumor part 102 while observing the image displayed on the display device 5.

At the subsequent step S207, while observing the displayed image, the surgeon performs marking by denaturing, with the diathermy knife 60 as the energy radiation device, mucous membrane tissue outside of the site determined to be the tumor part 102.

At the subsequent step S208, the surgeon resects the tumor using the denatured mucous membrane tissue as a guide.

This embodiment can achieve an effect same as the effect of the above-described first embodiment.

The present embodiment describes an exemplary method of performing the spectroscopic estimation processing on an image pickup signal based on the second light as the return light of the white light emitted as the first light, and performing marking and resecting of a tumor part based on a highlighted image generated by restructuring an image from the spectroscopic image. According to a modification, however, marking and resecting of a tumor part may be performed based on a highlighted image generated by another digital image processing.

For example, marking and resecting of a tumor part may be performed by generating a highlighted image through sharpness enhancement, partial brightness enhancement, color tone enhancement, or contrast enhancement on the image pickup signal based on the second light (return light), or by generating a highlighted image through a combination of these processes.

Figure 15:
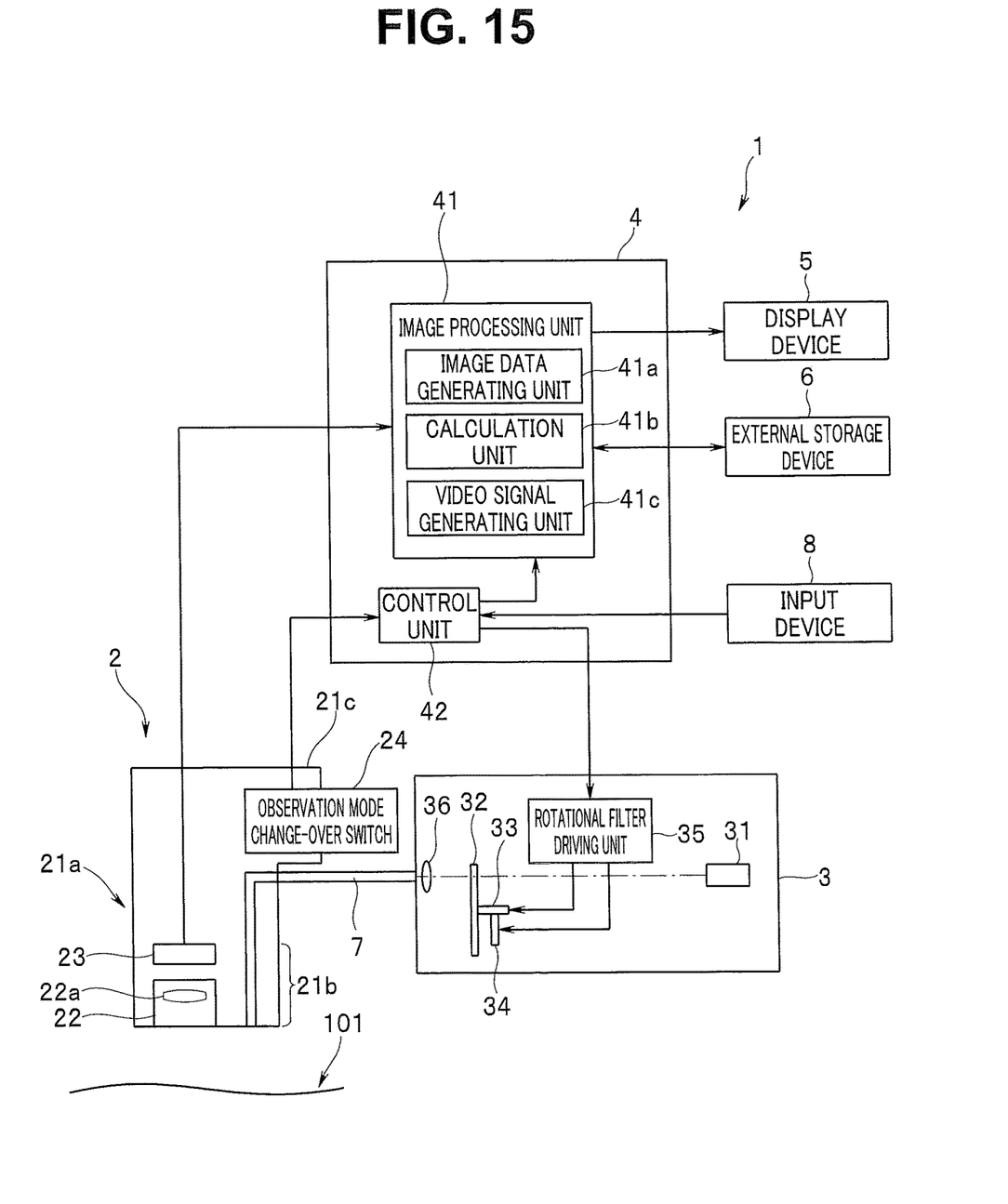
FIG. 15 is a diagram illustrating an exemplary configuration of a main part of the endoscope apparatus according to a third embodiment of the present invention.
Figure 16:
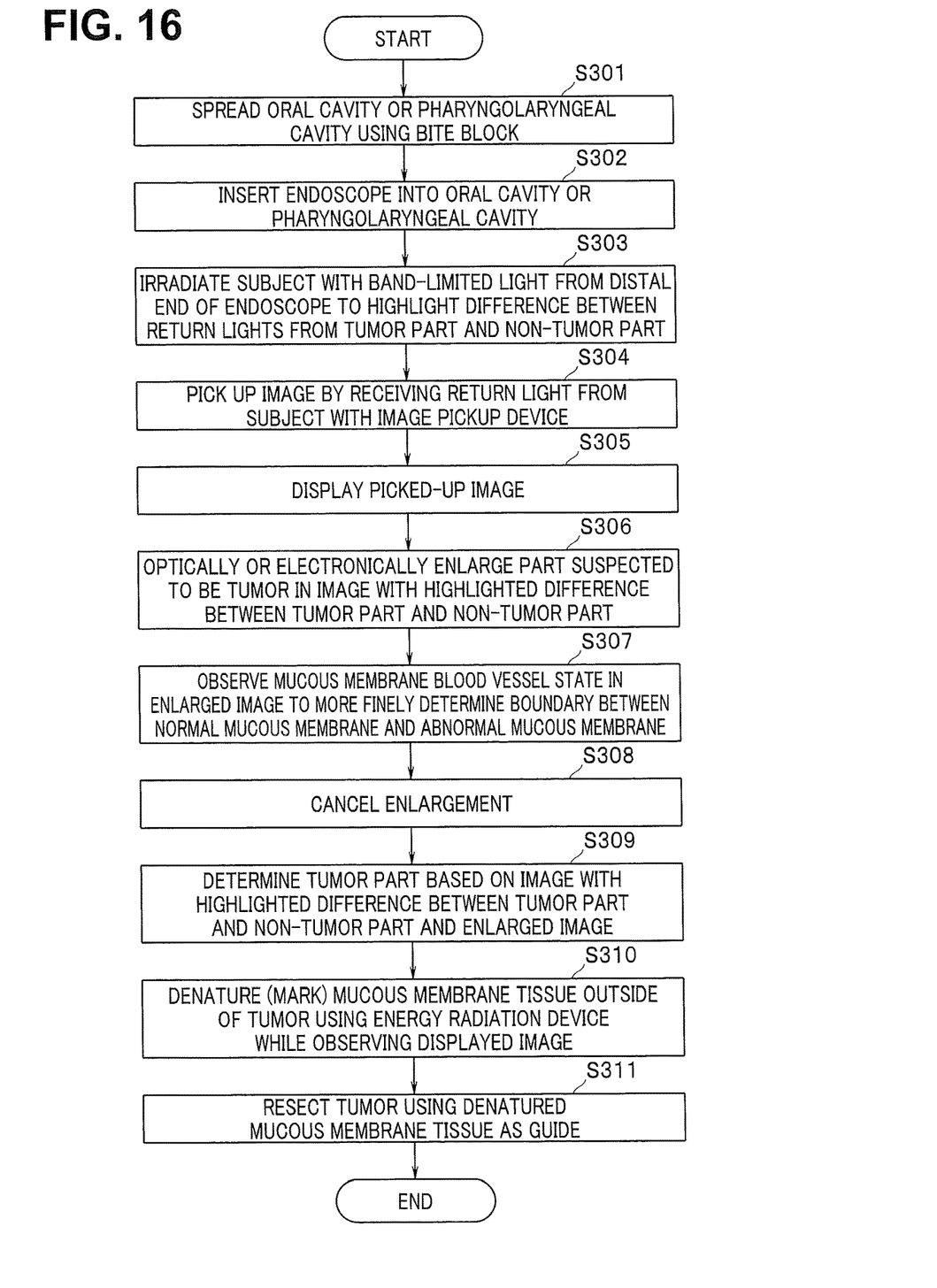
FIG. 16 is a flowchart illustrating an exemplary method of resecting a lesion in the laryngopharynx according to the third embodiment of the present invention.

FIGS. 15 and 16 illustrate a third embodiment of the present invention. FIG. 15 is a diagram illustrating an exemplary configuration of a main part of the endoscope apparatus, and FIG. 16 is a flowchart illustrating an exemplary method of resecting a lesion in a laryngopharynx. Note that, the present embodiment is different from the above-described first embodiment mainly in that the present embodiment includes, for example, an enlarged display step of generating and displaying an image obtained by enlarging an image of an observation target site of the subject. Description of any other feature same as the feature of the above-described first embodiment will be omitted as appropriate.

As illustrated in FIG. 15, the endoscope apparatus 1 according to the present embodiment includes a movable lens 22a in the objective optical system 22 to optically enlarge an image of the observation target site.

As illustrated in FIG. 16, in the resecting method according to the present embodiment, first at step S301, the surgeon spreads an oral cavity or a pharyngolaryngeal cavity using a bite block.

At the subsequent step S302, the surgeon selects, for example, the normal light observation mode, and inserts the insertion portion 21a of the endoscope 2 into the oral cavity or the pharyngolaryngeal cavity while observing a normal light image displayed on the display device 5.

Thereafter, the surgeon operates the observation mode change-over switch 24 of the endoscope 2 to select the narrow band light observation mode as the observation mode of the endoscope apparatus 1 and causes the display device 5 to display an image in which a difference between a tumor part and a non-tumor part is highlighted (steps S303 to S305).

That is, when the narrow band light observation mode is selected by the surgeon, an observation target site of the subject is irradiated with band-limited narrow band light (first light) from the distal end portion 21b of the endoscope 2 to highlight a difference between return lights from the tumor part and the non-tumor part (step S303).

Then, an image is picked up by receiving and picking up an image of, through the CCD 23 provided to the distal end portion 21b of the endoscope 2, return light (second light) generated at the observation target site through irradiation of the observation target site with the narrow band light (step S304).

Then, an image pickup signal based on the second light is processed by the image processing unit 41, and an image in which a site suspected to be a tumor is highlighted is displayed on the display device 5 (step S305).

At the subsequent step S306, the surgeon optically or electronically enlarges a part suspected to be a tumor in the image in which the difference between the tumor part and the non-tumor part is highlighted.

That is, at step S306, the surgeon causes, through an operation on, for example, a switch (not illustrated) provided to the endoscope 2, the movable lens 22a provided to the objective optical system 22 to move in an optical axis direction and optically enlarge an image of a part suspected to be a tumor. Alternatively, the surgeon electronically enlarges the image displayed on the display device 5 through an operation on the input device 8. Note that the image enlarged at the present step may be either an image in which the difference between the tumor part and the non-tumor part is highlighted, or a normal light image.

At the subsequent step S307, the surgeon observes a blood vessel state of mucous membrane in the enlarged image, and more finely determines a boundary between normal mucous membrane and abnormal mucous membrane.

At the subsequent step S308, the surgeon cancels the enlargement of the image through an operation on, for example, a switch provided to the endoscope 2, or an operation on the input device 8.

At the subsequent step S309, the surgeon comprehensively determines the tumor part while considering a result of determination based on the enlarged image and observing the image in which the difference between the tumor part and the non-tumor part is highlighted.

At the subsequent step S310, while observing the displayed image, the surgeon performs marking by denaturing, with the diathermy knife 60 as the energy radiation device, mucous membrane tissue outside of the site determined to be the tumor part 102.

At the subsequent step S311, the surgeon resects the tumor using the denatured mucous membrane tissue as a guide.

This embodiment can achieve an effect of more finely determining a tumor part through enlarged observation in addition to the effect of the above-described first embodiment.

Figure 17:
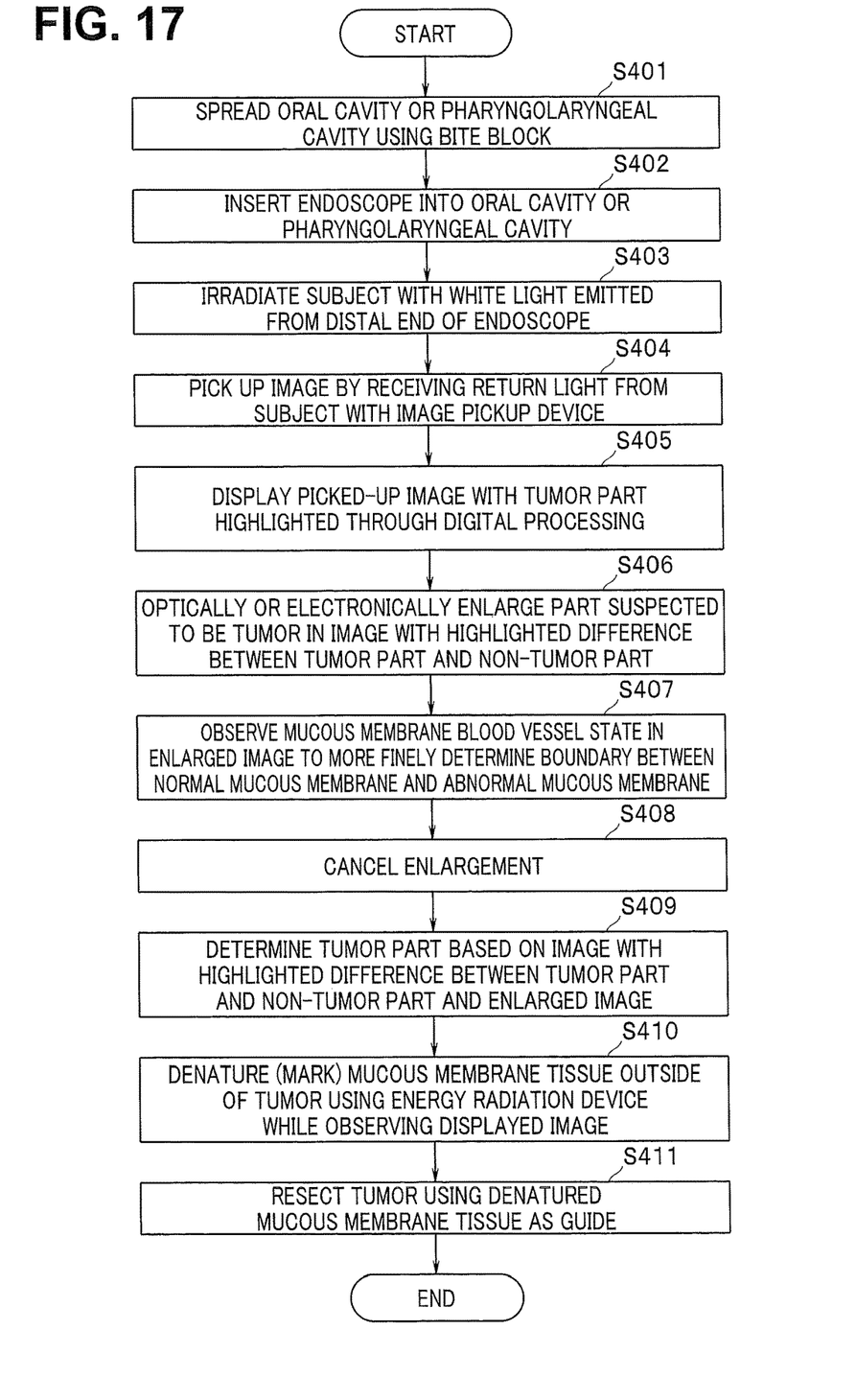
FIG. 17 is a flowchart illustrating an exemplary method of resecting a lesion in the laryngopharynx according to a fourth embodiment of the present invention.

FIG. 17 illustrates a fourth embodiment of the present invention, and is a flowchart illustrating an exemplary method of resecting a lesion in a laryngopharynx. Note that the present embodiment is different from the above-described third embodiment mainly in that the subject is irradiated with non-special light (white light) as the first light and an image obtained by picking up an image of return light (second light) from the subject is provided with digital processing to highlight a site suspected to be a tumor. Description of any other feature same as the feature of the above-described third embodiment will be omitted as appropriate.

As illustrated in FIG. 17, in the resecting method according to the present embodiment, first at step S401, the surgeon spreads an oral cavity or a pharyngolaryngeal cavity using a bite block.

At the subsequent step S402, the surgeon selects, for example, the normal light observation mode, and inserts the insertion portion 21a of the endoscope 2 into the oral cavity or the pharyngolaryngeal cavity while observing a normal light image displayed on the display device 5.

Thereafter, the surgeon operates the observation mode change-over switch 24 of the endoscope 2 to select the highlighted image observation mode as the observation mode of the endoscope apparatus 1, and causes the display device 5 to display an image in which a difference between a tumor part and a non-tumor part is highlighted (steps S403 to S405).

That is, when the highlighted image observation mode is selected by the surgeon, the observation target site of the subject is continuously irradiated with white light (first light) from the distal end portion 21b of the endoscope 2 (step S403).

Then, an image is picked up by receiving and picking up an image of, through the CCD 23 provided to the distal end portion 21b of the endoscope 2, the return light (second light) generated at the observation target site through irradiation of the observation target site with the white light (step S404).

Then, an image pickup signal based on the second light is digitally processed by the image processing unit 41, and an image in which a site suspected to be a tumor is highlighted is displayed on the display device 5 (step S405).

At the subsequent step S406, the surgeon optically or electronically enlarges a part suspected to be a tumor in the image in which the difference between the tumor part and the non-tumor part is highlighted.

At the subsequent step S407, the surgeon observes a blood vessel state of mucous membrane in the enlarged image, and more finely determines a boundary between normal mucous membrane and abnormal mucous membrane.

At the subsequent step S408, the surgeon cancels the enlargement of the image.

At the subsequent step S409, the surgeon comprehensively determines the tumor part while considering a result of determination based on the enlarged image and observing the image in which the difference between the tumor part and the non-tumor part is highlighted.

At the subsequent step S410, while observing the displayed image, the surgeon performs marking by denaturing, with the diathermy knife 60 as the energy radiation device, mucous membrane tissue outside of the site determined to be the tumor part 102.

At the subsequent step S411, the surgeon resects the tumor using the denatured mucous membrane tissue as a guide.

This embodiment can achieve an effect same as the effect of the above-described third embodiment.

Note that the present invention is not limited to the above-described embodiments and modifications, and various kinds of modifications and changes are possible and included in the technical scope of the present invention. For example, the above-described embodiments and modifications may be combined as appropriate.

In the above-described embodiments, description is exemplarily made on a pharyngolaryngeal cavity or the like as an observation target site not suitable for spray of a coloring agent, but the present invention is not limited thereto but is applicable to another observation target site.

In the above-described embodiments, description is made on the example in which a retractor is used as a bite block, but the present invention is not limited thereto. For example, various pharyngoscopes such as a bending pharyngoscope, or various kinds of other treatment tools such as various bite blocks may be used in place of the retractor.

In the above-described embodiments, description is made on the example in which a diathermy knife is used as an energy device for providing a tissue denatured portion, but the present invention is not limited thereto. For example, various kinds of laser treatment instruments, high frequency treatment instruments, thermal treatment instruments, and ultrasound treatment instruments may be used in place of the diathermy knife.

In the above-described embodiments, description is made on the example in which a diathermy knife is used as a device for resecting a tumor, but the present invention is not limited thereto. For example, various kinds of laser treatment instruments, high frequency treatment instruments, thermal treatment instruments, and ultrasound treatment instruments may be used in place of the diathermy knife.

What is claimed is:

1. A marking method comprising:
    inserting an endoscope into a subject;
    irradiating, with first light from the endoscope, an observation target site in the subject without spraying a coloring agent into the subject;
    picking up an image of, through the endoscope, second light generated at the observation target site through irradiation of the observation target site with the first light;
    displaying an image in which a site suspected to be a tumor is highlighted by highlight processing which generates the image based on the second light received through the endoscope; and
    providing a guide for a range suspected to be a tumor by providing a tissue denatured portion, the tissue denatured portion being provided by denaturing a tissue into a point, dotted-line, or line, around the site suspected to be a tumor by using an energy radiation device while observing the image in which the site suspected to be a tumor is highlighted wherein the tissue denatured portion is provided by flowing a high-frequency current to the subject through coagulation of protein by evaporating a fluid in cells of the tissue.

2. The marking method according to claim 1, wherein the first light is white light, and the image is an image provided with the highlight processing with a wavelength of the second light.

3. The marking method according to claim 1, wherein the first light is narrow-band visible light, and the image is an image in which a site suspected to be a tumor is highlighted by picking up an image of the second light.

4. The marking method according to claim 1, wherein the first light includes non-visible light, and the image is an image provided with the highlight processing with a wavelength of the second light.

5. The marking method according to claim 1, wherein the image is an image provided with the highlight processing with a particular wavelength among wavelengths of the second light.

6. The marking method according to claim 1, wherein the displaying of the image includes generating an image obtained by optically or electronically enlarging an image of the observation target site and displaying the enlarged image.

7. The marking method according to claim 6, wherein the providing of the point, dotted-line or line tissue denatured portion includes observing a blood vessel state of mucous membrane at the observation target site in the displayed enlarged image, and checking a boundary between normal mucous membrane and abnormal mucous membrane.

8. A resecting method comprising:
    the marking method according to claim 1; and
    resecting the site suspected to be a tumor along the tissue denatured portion.

9. The marking method according to claim 1, wherein the marking method is applied to an oral cavity or a pharyngolaryngeal cavity not suitable for spray of the coloring agent.

10. The resecting method according to claim 8, further comprising:
    switching an image displaying mode from a mode of displaying the image in which the site suspected to be a tumor is highlighted to a mode of displaying an image in which the site suspected to be a tumor is not highlighted,
    wherein the switching of the image displaying mode is subsequent to providing the tissue denatured portion, and prior to the resecting of the site suspected to be a tumor along the tissue denatured portion.

* * * * *